(12) United States Patent
Beckman et al.

(10) Patent No.: US 10,265,225 B2
(45) Date of Patent: Apr. 23, 2019

(54) DISPOSABLE ARTICLE INCLUDING AT LEAST ONE ELASTIC BONDED REGION

(71) Applicant: H.B FULLER COMPANY, St. Paul, MN (US)

(72) Inventors: Kristy J. Beckman, Dellwood, MN (US); David B. Malcolm, Maplewood, MN (US); Kevin P. Davis, Woodbury, MN (US); Yuanyan Gu, St. Paul, MN (US); Peter Remmers, Hamburg (DE); Thomas Wittkopf, Vogelsen (DE); Mark S. Kroll, Arden Hills, MN (US)

(73) Assignee: H.B. Fuller Company, St. Paul, MN (US)

( * ) Notice: Subject to any disclaimer, the term of this patent is extended or adjusted under 35 U.S.C. 154(b) by 734 days.

(21) Appl. No.: 14/849,226

(22) Filed: Sep. 9, 2015

(65) Prior Publication Data
US 2016/0067117 A1 Mar. 10, 2016

Related U.S. Application Data

(60) Provisional application No. 62/171,129, filed on Jun. 4, 2015, provisional application No. 62/048,066, filed
(Continued)

(51) Int. Cl.
*A61F 13/515* (2006.01)
*A61L 15/58* (2006.01)
(Continued)

(52) U.S. Cl.
CPC ...... *A61F 13/515* (2013.01); *A61F 13/15699* (2013.01); *A61F 13/15739* (2013.01); *A61F 13/4902* (2013.01); *A61F 13/49009* (2013.01); *A61F 13/4963* (2013.01); *A61L 15/58* (2013.01); *B32B 27/12* (2013.01);
(Continued)

(58) Field of Classification Search
CPC .. A61F 13/4963; A61F 13/515; A61F 13/539; A61F 2013/15569; A61F 2013/53908; A61F 2013/53916; A61F 2013/9395; A61F 2013/53958; A61F 2013/49063; A61F 2013/49065;
(Continued)

(56) References Cited

U.S. PATENT DOCUMENTS 4,543,099 A 9/1985 Bunnelle et al.
4,789,699 A 12/1988 Kieffer et al.
(Continued)

FOREIGN PATENT DOCUMENTS

EP 0802949 5/2003
EP 1411100 4/2004

OTHER PUBLICATIONS

Shawn W. Mowry, Ph.D., "New High-Efficiency Styrenic Block Copolymers, Tackifier for Adhesives"; Adhesives Magazine; Jan. 2009.
(Continued)

*Primary Examiner* — Catharine L Anderson
(74) *Attorney, Agent, or Firm* — Kirsten Stone; Kristi Halloran

(57) ABSTRACT

This invention claims a disposable article including at least two bonded regions, one of the regions has elastic properties; the other region is different from the first.

19 Claims, 3 Drawing Sheets

Related U.S. Application Data on Sep. 9, 2014, provisional application No. 62/048,047, filed on Sep. 9, 2014.

(51) Int. Cl.

| | | |
|---|---|---|
| *B32B 27/12* | (2006.01) | |
| *B32B 27/30* | (2006.01) | |
| *C09J 153/00* | (2006.01) | |
| *A61F 13/49* | (2006.01) | |
| *A61F 13/496* | (2006.01) | |
| *A61F 13/15* | (2006.01) | |
| *C09J 5/06* | (2006.01) | |
| *C09J 153/02* | (2006.01) | |
| *B32B 5/02* | (2006.01) | |
| *B32B 5/26* | (2006.01) | |
| *B32B 7/12* | (2006.01) | |
| *B32B 5/08* | (2006.01) | |
| *B32B 7/04* | (2019.01) | |
| *B32B 7/14* | (2006.01) | |
| *B32B 37/12* | (2006.01) | |
| *B32B 38/00* | (2006.01) | |

(52) U.S. Cl.
CPC ............... *B32B 27/302* (2013.01); *C09J 5/06* (2013.01); *C09J 153/00* (2013.01); *C09J 153/02* (2013.01); *C09J 153/025* (2013.01); *A61F 2013/1591* (2013.01); *A61F 2013/49022* (2013.01); *A61F 2013/49049* (2013.01); *B32B 5/022* (2013.01); *B32B 5/08* (2013.01); *B32B 5/26* (2013.01); *B32B 7/045* (2013.01); *B32B 7/12* (2013.01); *B32B 7/14* (2013.01); *B32B 37/1292* (2013.01); *B32B 2037/1215* (2013.01); *B32B 2038/0072* (2013.01); *B32B 2255/02* (2013.01); *B32B 2255/26* (2013.01); *B32B 2262/0253* (2013.01); *B32B 2262/0276* (2013.01); *B32B 2262/04* (2013.01); *B32B 2262/06* (2013.01); *B32B 2262/14* (2013.01); *B32B 2305/20* (2013.01); *B32B 2307/51* (2013.01); *B32B 2307/54* (2013.01); *B32B 2307/726* (2013.01); *B32B 2437/00* (2013.01); *B32B 2535/00* (2013.01); *B32B 2555/02* (2013.01); *C09J 2400/263* (2013.01); *C09J 2453/00* (2013.01)

(58) Field of Classification Search
CPC ...... A61F 2013/49066; A61F 13/49009; A61F 13/49011; A61F 13/49012
See application file for complete search history.

(56) References Cited

U.S. PATENT DOCUMENTS

| | | | |
|---|---|---|---|
| 5,149,741 A | 9/1992 | Alper et al. | |
| 5,536,563 A | 7/1996 | Shah et al. | |
| 6,025,071 A | 2/2000 | Cameron | |
| 6,103,814 A | 8/2000 | vanDrongelen | |
| 6,120,887 A * | 9/2000 | Werenicz | A61F 13/51405 156/334 |
| 6,162,859 A | 12/2000 | Lu | |
| 6,184,285 B1 | 2/2001 | Hatfield et al. | |
| 6,245,050 B1 | 6/2001 | Odorzynski et al. | |
| 6,497,696 B1 | 12/2002 | Freiburger et al. | |
| 6,503,239 B1 | 1/2003 | Bruemmer-Prestley et al. | |
| 6,533,765 B1 | 3/2003 | Blaney et al. | |
| 6,582,829 B1 | 6/2003 | Quinn et al. | |
| 6,702,798 B2 | 3/2004 | Christoffel et al. | |
| 6,967,178 B2 * | 11/2005 | Zhou | A61F 13/15593 428/343 |
| 7,000,260 B2 | 2/2006 | Rajala et al. | |
| 7,015,155 B2 | 3/2006 | Zhou et al. | |
| 7,207,979 B2 | 4/2007 | Price et al. | |
| 7,297,139 B2 | 11/2007 | Price et al. | |
| 7,316,842 B2 | 1/2008 | Zhou et al. | |
| 7,329,621 B2 | 2/2008 | Collier et al. | |
| 7,439,301 B2 | 10/2008 | Handlin, Jr. | |
| 7,621,900 B2 | 11/2009 | Van Gompel et al. | |
| 7,651,765 B2 | 1/2010 | De Keyzer | |
| 7,717,893 B2 | 5/2010 | Hird et al. | |
| 7,749,211 B2 | 7/2010 | Van Gompel et al. | |
| 7,795,336 B2 | 9/2010 | Paul et al. | |
| 7,799,863 B2 | 9/2010 | He et al. | |
| 7,887,526 B2 | 2/2011 | Van Gompel et al. | |
| 7,923,505 B2 | 4/2011 | Zhou et al. | |
| 8,147,476 B2 | 4/2012 | Veith et al. | |
| 8,163,824 B2 | 4/2012 | Okazaki et al. | |
| 8,257,334 B2 * | 9/2012 | Buell | A61F 13/496 2/400 |
| 8,277,430 B2 | 10/2012 | Tabor et al. | |
| 8,324,309 B2 | 12/2012 | Dubois | |
| 8,377,023 B2 * | 2/2013 | Sawyer | A61F 13/49012 604/385.22 |
| 8,450,555 B2 | 5/2013 | Nhan et al. | |
| 8,664,469 B2 | 3/2014 | Veith et al. | |
| 8,920,400 B2 | 12/2014 | Veith | |
| 9,011,401 B2 * | 4/2015 | Kamiyama | A61F 13/49011 604/385.01 |
| 9,056,975 B2 | 6/2015 | Chapman et al. | |
| 2003/0168165 A1 | 9/2003 | Hatfield et al. | |
| 2004/0162394 A1 | 8/2004 | Bunnelle et al. | |
| 2006/0246804 A1 | 11/2006 | Thomas et al. | |
| 2007/0117934 A1 | 5/2007 | He et al. | |
| 2008/0038982 A1 | 2/2008 | Motomura | |
| 2008/0076860 A1 | 3/2008 | Ahmed | |
| 2008/0081858 A1 | 4/2008 | Okazaki | |
| 2009/0088718 A1 | 4/2009 | Toyoshima | |
| 2012/0149827 A1 | 6/2012 | Hu et al. | |
| 2012/0226250 A1 | 9/2012 | Nobuya | |
| 2013/0202787 A1 | 8/2013 | Hu et al. | |
| 2013/0225020 A1 | 8/2013 | Flood et al. | |
| 2013/0299731 A1 | 11/2013 | Wright | |
| 2014/0357145 A1 | 12/2014 | Remmers | |
| 2014/0364532 A1 | 12/2014 | Dubois et al. | |
| 2015/0017868 A1 | 1/2015 | Stafeil et al. | |
| 2016/0067116 A1 | 3/2016 | Beckman | |
| 2016/0068721 A1 | 3/2016 | Malcolm | |
| 2016/0271291 A1 | 9/2016 | Mansour | |
| 2016/0376482 A1 | 12/2016 | Morgeneyer | |
| 2017/0157888 A1 | 6/2017 | Ikishiru et al. | |

OTHER PUBLICATIONS

Kraton Innovations, "MD1648:A New Addition to the Kraton™ ERS Polymer Family", Market Launch Package. May 2014, pp. 1-20.

Haso USA Inc. Product Brochure, "Haso Underwear" Body Form 360○™.

Benedek, Pressure-Sensitive Adhesives and Applications, 2nd ed., Ch.6, 2004.

"Section III: Physical Properties of Monomers and Solvents." Polymer Handbook, By E.H. Immergut et al., 4th Ed., Wiley, 2005, pp. 34-36.(Year:2005).

"Temperature and Pressue Dependence of Viscosity." polymer Testing, by Wolfgang Grellmann and Sabine Seidler, Hanser Publishers, 2007, pp. 46-46.

* cited by examiner

DISPOSABLE ARTICLE INCLUDING AT LEAST ONE ELASTIC BONDED REGION

This application claims priority to and benefit of provisional filed patent application No. 62/048,047 and 62/048,066 filed on Sep. 9, 2014 and provisional patent application No. 62/171,129 filed on Jun. 4, 2015.

BACKGROUND

Adhesives are often used to bond substrates together. In the area of industrial adhesives, hot melt adhesives are commonly used to bond together a wide variety of articles including disposable absorbent articles comprising nonwoven substrates e.g. diapers, training paints, surgical garments, swim wear, absorbent underpants, adult incontinence products, sanitary napkins and medical dressings (e.g. wound care products).

There can be multiple hot melt adhesives used in the manufacture of a disposable absorbent article. For example, in the manufacture of a disposable diaper, hot melt adhesives are used for construction (e.g. bonding the backsheet to the nonwoven and optionally the absorbent pad), elastic attachment (e.g. bonding the elastic material to the backsheet in (or example the leg or waist area), and for core stabilization (e.g. applying a hot melt adhesive to the absorbent core to increase the strength of the core).

Hot melt adhesives can also be used to form elastic composites that are useful in disposable articles. Currently, elastic composites are often formed in a 5-layer configuration including the following layers: nonwoven, hot melt adhesive, elastic material, hot melt adhesive, nonwoven. The hot melt adhesive bonds the non adhesive elastic to the nonwoven to form a composite.

Alternatively, a hot melt adhesive with elastic properties can replace the elastic material to form simplified composites that can impart stretch to various portions of the disposable article.

SUMMARY

In one aspect, the invention includes a disposable article including at least two adjacent bonded regions, the first bonded region, including: a first and second substrate; and an elastic hot melt adhesive composition between the first and second substrates thereby bonding the first and second substrates to each other; the elastic hot melt adhesive composition having a viscosity of less than about 15,000 cps at 350° F. and a set after 50% hysteresis of no greater than about 20%; the second bonded region comprising: a first and second substrate; and a hot melt adhesive composition between the first and second substrates thereby bonding the first and second substrates to each other, the second bonded region having properties different from the first.

In one embodiment, the at least two adjacent bonded regions comprise the same elastic hot melt adhesive applied at different coat weights. In another embodiment, the second bonded region comprises a second hot melt adhesive composition different from the elastic hot melt adhesive composition. In still another embodiment, the two different hot melt adhesives are applied to the substrate using two different application methods.

In a different embodiment, the disposable article is a disposable absorbent article.

In one embodiment, at least one of the substrates is nonwoven. In another embodiment, the nonwoven is airlaid, carded and hydroentangled. In a different embodiment, the nonwoven is extensible to greater than 100% in the cross web direction.

In one embodiment, the at least two adjacent bonded regions are used in a application selected from the group consisting of fastening ear, waist band, belly band and side panel. In a different embodiment, three adjacent bonded regions make up the fastening ear; the three adjacent bonded regions comprising an elastic bonded region between two second bonded regions.

In one embodiment, the disposable article is selected from the group consisting of diaper, absorbent undergarment, feminine hygiene product and medical bandage.

In another embodiment, the disposable article is an absorbent undergarment including adjacent bonded regions throughout the absorbent undergarment, the adjacent bonded regions comprising elasticized regions alternating with second bonded regions.

In one embodiment, the elastic hot melt adhesive composition includes about 30% by weight to about 60% by weight of one or more styrene block copolymers wherein the one or more styrene block copolymers has an average styrene content of at least about 30% by weight and an average MFR (200° C./5 kg) of no less than about 20, greater than about 10% of a plasticizer and, a tackifying agent.

In another embodiment, the elastic hot melt adhesive composition includes a tackifying agent that is a hydrocarbon resin with about 5% to about 20% by weight of aromatic content, and; a plasticizer that is a naphthenic oil. In a different embodiment, the average styrene content of the one or more styrene block copolymers is at least about 40% by weight. In one embodiment, the one or more styrene block copolymers has an average MFR (200° C./5 kg) of no less than about 30.

In one embodiment, at least one of the hot melt adhesives is applied to the substrate using an application method selected from the group consisting of slot and non contact coating. In another embodiment, at least one of the hot melt adhesives is applied to the substrate using an application method selected from the group consisting of screen printing, spraying, comb shim slot and gravure roll.

In another aspect, the invention claims a disposable article including at least two elastic regions, the elastic regions including: at least one substrate; and an elastic hot melt adhesive composition bonded to the substrate wherein the hot melt adhesive composition provides elasticity to the bonded area; the elastic hot melt adhesive composition having a viscosity of less than about 15,000 cps at 350° F. and a set after 50% hysteresis of no more than about 20%.

In a different aspect, the invention includes a disposable article including at least one layered bonded region, the layered bonded region including: a first substrate, an elastic hot melt adhesive composition coated in a continuous coating on the first substrate, a second hot melt adhesive composition coated in a discontinuous manner on the elastic hot melt adhesive, and a second substrate; wherein the second substrate is bonded to the elastic hot melt adhesive composition through the second hot melt adhesive composition; the elastic hot melt adhesive composition having a viscosity of less than about 15,000 cps at 350° F. and a set after 50% hysteresis of no more than about 20%.

DETAILED DESCRIPTION

Figure 1:
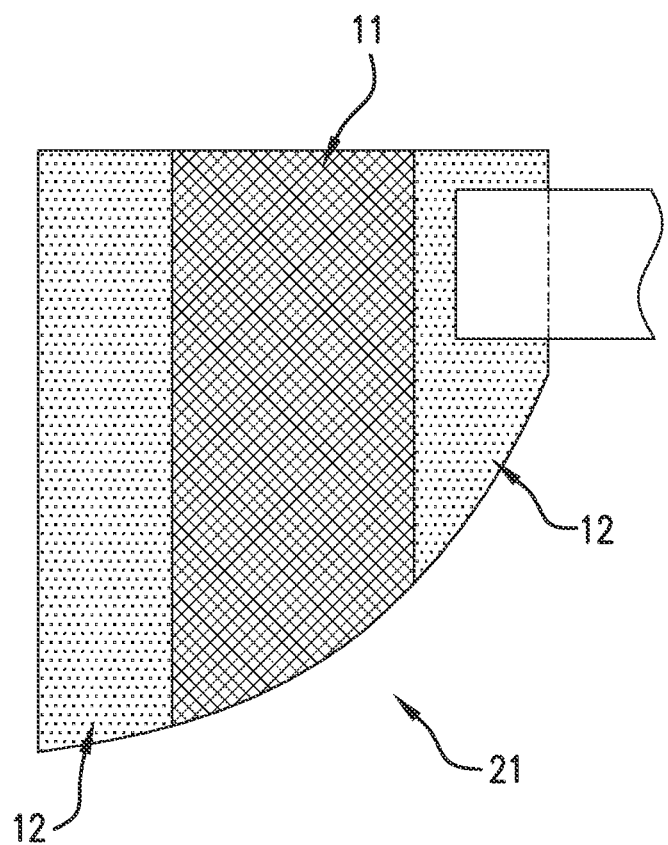
FIG. 1 is a top view of a diaper fastening tab comprising three adjacent bonded regions.

Applicants have discovered hot melt adhesive compositions that can be used to form elastic regions that are useful in disposable articles (e.g. disposable absorbent articles). The compositions have good elastic recovery and a viscosity of less than about 15,000 cps at 177° C. (350° F.). The low viscosity makes it possible to apply the hot melt adhesive at a high line speed and register provide zoned application to only those areas requiring elastic performance. The low viscosity further makes it possible to apply the hot melt adhesive within the disposable article manufacturing line. The low viscosity of the hot melt adhesive composition gives flexibility to the user, resulting in the ability to create elastic bonded regions.

Disposable Article.

Adjacent Bonded Regions

The disposable article can comprise at least two bonded regions, the at least two bonded regions can be adjacent to each other. By adjacent, it is meant that the two bonded regions are side by side. The two adjacent bonded regions can slightly overlap each other. At least one of the adjacent bonded regions is bonded with an elastic hot melt adhesive. The second region can be bonded with an elastic hot melt adhesive or alternatively is bonded with a second hot melt adhesive.

The second hot melt adhesive can be used to introduce additional properties into the article e.g. stiffness (i.e. by use an adhesive with a higher modulus as compared to the elastic hot melt adhesive), breathability, lower cost, improved adhesion and/or improved creep resistance.

The second hot melt adhesive can be used to control the extent to which the elastic hot melt adhesive can elongate by varying the width of the elastic bonded regions relative to the second bonded regions.

The at least two adjacent bonded regions are different from each other. In one embodiment, the same elastic hot melt adhesive applied at two different coat weights is used to construct two adjacent bonded regions.

The elastic region can include a first substrate and a hot melt adhesive composition. The hot melt adhesive composition imparts elasticity to the first substrate.

Alternatively, the elastic region can include a first substrate, a second substrate and an elastic hot melt adhesive composition. The elastic hot melt adhesive composition is present between the first and second substrate, permanently bonding the substrates to each other and providing elasticity in the bonded area.

Layered Bonded Region

In a different embodiment, the invention includes a layered bonded region. In this embodiment, the elastic hot melt adhesive can be coated in a continuous film on a first substrate and then a second hot melt adhesive is applied in a discontinous manner directly on top of the elastic hot melt adhesive. The second hot melt can then be used to bond the second substrate to the elastic hot melt adhesive to form a composite with four layers: first substrate, elastic hot melt adhesive film, discontinuous coating of a second hot melt adhesive, and second substrate.

Adjacent/Layered Bonded Region/s

One of the substrates can be a nonwoven. Any nonwoven can be used. The nonwoven can contain fibers made from one or more polymers (e.g. PET (polyethylene terephthalate), PBT (polybutylene terphthalate), nylon, polypropylene and polyethylene, one or more natural fibers (e.g. rayon cellulose, cotton cellulose, hemp and viscose) or combinations thereof. The nonwoven can be formed by a number of different methods, including e.g. airlaid, wetlaid, spunbond or meltblown. The fibers can be carded (e.g. run through a comb) so that they are oriented in a particular direction. The webs can be bonded together in any manner including e.g., hydroentangled, chemical bonded, needle punched or thermally bonded. In one embodiment, the nonwoven is comprised of a blend of polypropylene and polyethylene fibers which are airlaid, carded and hydroentangled. In another embodiment, the nonwoven may be a self-elastic. This is accomplished by incorporation of elastic fibers into the nonwoven, or by incorporating absorbed elastic material to improve elasticity. Hot melt adhesives described herein can be used in conjunction with elastic nonwoven to augment the elastic performance of the composite.

Alternatively one of the substrates can be nonwoven and the other can be a polymer film. Any polymer film can be used. The polymer film can be selected from the group consisting of polyethylene, polypropylene, polyethylene copolymers, polypropylene copolymers, and PET.

The first and second substrate can be nonwoven. The nonwoven can have a basis weight of less than 40 gsm (grams per square meter), less than 35 gsm, or even less than about 30 gsm. The nonwoven can be extensible to greater than 100% in the cross-web direction. At least one of the substrates is selected from the group consisting of nonwoven and polymer film.

Various post treatments, such as treatment with grooved rolls i.e. activation can be used to adjust the mechanical properties (e.g. extensibility) of the composite.

The elastic hot melt adhesive can be applied to the first and/or second substrate using a variety of applicator methods including slot coating, non-contact coating, comb shim coating, spraying including, e.g., spiral spraying and random spraying, screen printing, foaming (e.g., using chemical foaming agents or a Nordson FoamMelt® Dispensing System), engraved roller, gravure roller, extrusion and meltblown.

The elastic hot melt adhesive can be applied to one substrate.

Alternatively, the elastic hot melt adhesive can be applied to the first substrate and then contacted by the second substrate to form the bonded region. Pressure, tension and/or line speed can be used to aid in forming the bonded region. The bonded regions can be formed within a disposable article manufacturing process. Alternatively, the bonded regions are formed prior to the disposable article manufacturing process.

Elastic Hot Melt Adhesive Composition

The elastic hot melt adhesive can be a pressure sensitive (i.e. exhibit tack at room temperature) hot melt adhesive. The elastic hot melt adhesive composition can be light in color and can have good thermal stability. In a cooled film, the hot melt adhesive can be clear i.e. translucent or alternatively the hot melt adhesive can be opaque. The elastic hot melt adhesive can have an Initial Molten Gardner Color after manufacturing of less than about 3, or even less than about 2. Alternately, the elastic hot melt adhesive can be pigmented to an opaque color such as e.g. pink, blue, white, gray, etc.

The elastic hot melt adhesive composition has low viscosity at application temperature. The viscosity is no greater than about 15,000 cps at around 177° C. (350° F.), no greater than about 10,000 cps at around 177° C. (350° F.), no greater than about 7,500 cps at around 177° C. (350° F.), or even no greater than about 5,000 cps at 177° C. (350° F.). The elastic hot melt adhesive composition gives a set after 50% hysteresis of no greater than about 20%, no greater than about 12%, no greater than about 10% or even no greater than about 8% when tested according to the 2-Peak Hysteresis Test Method.

The elastic hot melt adhesive composition provides good adhesion when tested according to the Peel Force Test Method. In some embodiments, the elastic hot melt adhesive can have a peel adhesion of greater than about 100 grams, greater than about 200 grams, or even greater than about 300 grams.

The elastic hot melt adhesive composition can include one or more styrene block copolymers, a tackifying agent, and greater than about 15% by weight of a plasticizer.

The elastic hot melt adhesive composition can have a viscosity curve with a Viscosity Ratio (i.e. Viscosity @ 149° C. (300° F.) (cps)/Viscosity @ 177° C. (350° F.) that is less than about 7, less than about 6, less than about 5, or even less than about 4. A low viscosity ratio can indicate improved machining at high line speeds as the hot melt adhesive does not gain viscosity as quickly as it cools.

The elastic hot melt adhesive composition can include a tackifying agent with at least some aromatic content and a plasticizer such as napthenic oil.

Styrene Block Copolymers

The elastic hot melt adhesive includes one or more styrene block copolymers.

A styrene block copolymer includes an aromatic vinyl polymer block and a conjugated diene polymer block, a hydrogenated conjugated diene polymer Hock, or a combination thereof. The blocks can be arranged in a variety of configurations including, e.g., linear, branched, radial, star block, and combinations thereof. The aromatic vinyl polymer block can be derived from a variety of aromatic vinyl compounds including, e.g., styrene, alpha-methylstyrene, beta-methylstyrene, o-, m-, p-methylstyrene, t-butylstyrene, 2,4,6-trimethylstyrene, monofluorostyrene, difluorostyrene, monochlorostyrene, dichlorostyrene, methoxystyrene, 1,3-vinylnaphthalene, vinylanthracene, indene, acenaphthylene, and combinations thereof. The diene polymer block can be derived from a variety of diene-containing compounds including, e.g., isoprene, butadiene, hexadiene, 2,3-dimethyl-1,3-butadiene, 1,3-pentadiene, and hydrogenated versions thereof, and combinations thereof.

Useful styrene block copolymers include, e.g., diblock, triblock and multiblock copolymers including, e.g., styrene-butadiene, styrene-butadiene-styrene, styrene-isoprene, styrene-isoprene-styrene, styrene-ethylene/butene, styrene-ethylene/butene-styrene, styrene-ethylene/propylene, styrene-ethylene/propylene-styrene, styrene-ethylene-ethylene/propylene-styrene, and combinations thereof.

The one or more styrene block copolymers have an average styrene content of at least about 30%, at least about 35%, at least about 40%, or even from about 35% to about 45% by weight.

As an example, if a hot melt composition comprises two styrene block copolymers A and B. Polymer A is present at 25 weight % with a styrene content of 35% and polymer B is present at 25 weight % with a styrene content of 45 weight %. The average styrene content of the one or more styrene block copolymers is calculated in the following way: 0.5 (35)+0.5 (45)=40 weight %.

The one or more styrene block copolymers have an average Melt Flow Rate (MFR) according to ASTM D 1238 (200° C./5 kg) in dg/min of no less than about 20, no less than about 25, or even no less than about 30. The average MFR of the styrene block copolymers is calculated in a similar manner as the average styrene content.

The elastic hot melt adhesive can include at least one styrene block copolymer with a styrene content of at least about 40% by weight.

The composition has a total styrene block copolymer content of greater than 40% by weight, greater than 45% by weight, from about 30% to about 60% by weight, from about 35% to about 55% by weight, or even from about 40% to about 50% by weight.

The styrene block copolymers can be pure tri-block copolymers containing no di-block. Alternately, the styrene block copolymer can include a portion of di-block. The styrene block copolymer can include diblock content of greater than 30%.

Useful styrene block copolymers include VECTOR 6241 (Linear, styrene-butadiene-styrene, pure triblock copolymer, 43 wt % styrene, MFR (200° C./5 kg)=23 dg/min), VECTOR 8508 (Linear, styrene-butadiene-styrene, pure triblock copolymer, 29 wt % styrene, MFR (200° C./5 kg)=12 dg/min and VECTOR 4411 (Linear, styrene-isoprene-styrene, pure triblock copolymer, 44 wt % styrene, MFR (200° C./15 kg)=40 dg/in) all available from TSRC Dexco (Houston, Tex.) and GLOBALPRENE 3545 (Linear, styrene-butadiene-styrene block copolymer, 63% diblock, 45 wt % styrene, MFR (190° C./5 kg)=55) available from LCY CHEMICAL CORP. (Taipei, Taiwan). Another useful styrene block copolymer includes KRATON FG 1901 G (Linear, styrene-ethylene/butylene-styrene, 30 wt % styrene, with 1.7% bound maleic anhydride) available from KRATON POLYMERS U.S. LLC (Houston, Tex.).

Tackifying Agent

The elastic hot melt adhesive can include a tackifying agent. The tackifying agent can be fluid or solid at room temperature. Suitable classes of tackifying agents include, e.g., aromatic, aliphatic and cycloaliphatic hydrocarbon resins, mixed aromatic and aliphatic modified hydrocarbon resins, aromatic modified aliphatic hydrocarbon resins, and hydrogenated versions thereof; terpenes, modified terpenes and hydrogenated versions thereof; natural rosins, modified rosins, rosin esters, and hydrogenated versions thereof; low molecular weight polylactic acid; and combinations thereof. Examples of useful natural and modified rosins include gum rosin, wood rosin, tall oil rosin, distilled rosin, hydrogenated rosin, dimerized rosin and polymerized rosin. Examples of useful rosin esters include e.g., glycerol esters of pale wood rosin, glycerol esters of hydrogenated rosin, glycerol esters of polymerized rosin, pentaerythritol esters of natural and modified rosins including pentaerythritol esters of pale wood rosin, pentaerythritol esters of hydrogenated rosin, pentaerythritol esters of tall oil rosin, and phenolic-modified pentaerythritol esters of rosin.

Useful tackifying agents are commercially available under a variety of trade designations including, e.g., the ESCOREZ series of trade designations from Exxon Mobil Chemical Company (Houston, Tex.) including ESCOREZ 5400 (1% aromatic content), ESCOREZ 5600 (9.8% aromatic content), ESCOREZ 5690 (10% aromatic content), ESCOREZ 5615 (9.9% aromatic content), the EASTOTAC series of trade designations from Eastman Chemical (Kingsport, Tenn.) including EASTOTAC H-100R and EASTOTAC H-1.0L, and the WINGTACK series of trade designations from Cray Valley HSC (Exton, Pa.) including WINGTACK 86, WINGTACK EXTRA, and WINGTACK 95 and the PICCOTAC and KRISTALEX series of trade designations from Eastman Chemical Company (Kingsport, Tenn.) including, PICCOTAC 8095 and KRISTALEX 3100.

The elastic hot melt adhesive can be free from end block resin that has a melting point greater than about 130° C.

The elastic hot melt adhesive composition can include at least one tackifying agent with aromatic content. The tackifying agent can have an aromatic content of greater than 5%, greater than 20%, greater than 50%, from about 5% to about 20% by weight, or even from about 8% to about 15% by weight.

The composition can include a tackifying agent with a melt point of less than 100° C., or even less than 95° C.

The elastic hot melt adhesive composition can include at least about 20% by weight, at least about 25% by weight, from about 10% by weight to about 50% by weight, from about 15% by weight to about 40% by weight, or even from about 20% by weight to about 37% by weight tackifying agent.

Plasticizer

The elastic hot melt adhesive composition can include a plasticizer. Suitable plasticizers include, e.g., naphthenic oils, paraffinic oils (e.g., cycloparaffin oils), mineral oils, phthalate esters, adipate esters, olefin oligomers (e.g., oligomers of polypropylene, polybutene, and hydrogenated polyisoprene), polybutenes, polyisoprene, hydrogenated polyisoprene, polybutadiene, benzoate esters, animal oil, plant oils (e.g. castor oil, soybean oil high oleic soy oil), derivatives of oils, glycerol esters of fatty acids, polyesters, polyethers, lactic acid derivatives and combinations thereof.

Useful commercially available plasticizers include CALSOL 550 naphthenic oil from Calumet Specialty Products Partners, LP (Indianapolis, Ind.), KAYDOL OIL mineral oil from Sonneborn (Tarrytown N.Y.) PARAPOL polybutene from Exxon Mobil Chemical Company (Houston, Tex.), OPPANOL polyisobutylene from BASF (Ludwigsjhafen, Germany), KRYSTOL 550 mineral oil from Petrochem Carless Limited (Surrey, England), PURETOL 35 and 15 both mineral oils from Petro Canada Lubricants Inc. (Mississauga, Ontario) and PLENISH from Pioneer DuPont.

The plasticizer can be a naphthenic oil. Alternately, the plasticizer includes aromatic or naphthenic groups.

The plasticizer can be present in the elastic hot melt adhesive composition in an amount of at least about 10%, at least about 15% by weight, at least about 18% by weight, from about 10% to about 30% by weight, or even from about 15% to about 25% by weight.

Wax

The elastic hot melt adhesive composition can include a wax. Useful classes of wax include, e.g., paraffin waxes, microcrystalline waxes, high density low molecular weight polyethylene waxes, by-product polyethylene waxes, polypropylene waxes, Fischer-Tropsch waxes, oxidized Fischer-Tropsch waxes, functionalized waxes such as acid, anhydride, and hydroxy modified waxes, animal waxes, vegetable waxes (e.g. soy wax) and combinations thereof. Useful waxes are solid at room temperature and preferably have a Ring and Ball softening point of from 50° C. to 170° C. Useful waxes are commercially available from a variety of suppliers including EPOLENE N and C series of trade designations from Westlake Chemical Corporation (Houston, Tex.) including e.g. EPOLENE N-21 and the LICOCENE series of trade designations from Clariant International Ltd. (Muttenz, Switzerland) including e.g. TP LICOCENE PP 6102.

The elastic hot melt adhesive composition can include no greater than about 8% by weight, no greater than about 5% by weight, from about 1% by weight to about 7.5% by weight, or even from about 1% to about 5% by weight wax.

Additional Components

The elastic hot melt adhesive composition optionally includes additional components including but not limited to, e.g., foaming agents, stabilizers, antioxidants, additional polymers (e.g. olefin based polymers (e.g. propylene homopolymers, propylene copolymers, ethylene homopolymers, ethylene copolymers functionalized polymers such as acid, anhydride, and hydroxy modified polymers), amorphous poly-alpha olefins, polyethylene copolymers), adhesion promoters, ultraviolet light stabilizers, corrosion inhibitors, odor absorbers/neutralizers, colorants (e.g., pigments (e.g. titanium dioxide, carbon black, and mixtures thereof) and dyes), fragrances, fillers (e.g. nano particles, calcium carbonate, clay, talc, fumed silica), surfactants, wetness indicators, superabsorbents, coextrusion coatings, processing aids and combinations thereof.

The hot melt adhesive comprises from about 0.1 to about 2.0% by weight pigment, or even from about 0.1 to about 0.5% by weight pigment.

Useful antioxidants include, e.g., pentaerythritol tetrakis [3,(3,5-di-tert-butyl-4-hydroxyphenyl)propionate], 2,2'-methylene bis(4-methyl-6-tert-butylphenol), phosphites including, e.g., tris-(p-nonylphenyl)-phosphite (TNPP) and bis(2,4-di-tert-butylphenyl)4,4'-diphenylene-diphosphonite, di-stearyl-3,3'-thiodipropionate (DSTDP), and combinations thereof. Useful antioxidants are commercially available under a variety of trade designations including, e.g., the IRGANOX series of trade designations including, e.g., IRGANOX 1010, IRGANOX 565, and IRGANOX 1076 hindered phenolic antioxidants and IRGAFOS 168 phosphite antioxidant, all of which are available from BASF Corporation (Florham Park, N.J.), and ETHYL 702 4,4'-methylene bis(2,6-di-tert-butylphenol). When present, the elastic hot melt adhesive composition preferably includes from about 0.1% by weight to about 2% by weight antioxidant.

Disposable Article

The bonded regions of this invention can be incorporated into any suitable disposable article including personal care garments, medical garments and industrial worker garments.

The bonded regions of this invention are useful in a variety of applications and constructions to improve comfort and fit including disposable absorbent articles including, e.g., diapers, training paints, swim wear, absorbent undergarments (e.g. adult incontinence products), sanitary napkins, medical dressings (e.g., wound care products and bandages), surgical pads, medical gowns, caps, gloves, drapes, face masks, laboratory coats, coveralls, meat-packing products, and components of absorbent articles including, e.g., an absorbent element, absorbent cores, impermeable layers (e.g., backsheets), tissue (e.g., wrapping tissue), acquisition layers and woven and nonwoven web layers (e.g., top sheets, absorbent tissue).

Disposable Absorbent Article

The bonded regions of this invention are useful for elasticizing many areas of disposable absorbent articles including leg cuffs, waist portions, belly bands, side panels and fastening tabs/ears. The elastic composite of this invention can further be used to elasticize any portion of the disposable article or even the entire disposable article.

Fastening Tab/Ears

The adjacent bonded regions of this invention are useful in elasticizing the fastening tab/ear of a disposable absorbent article.

In one embodiment (FIG. 1), the fastening tab (21) comprises three adjacent bonded regions. An elastic bonded region (11) with a second bonded region on either side (12).

Each bonded region comprises a first and second substrate and a hot melt adhesive composition between the first and second substrates thereby bonding the first and second substrates together. The elastic region comprises an elastic hot melt adhesive. The second bonded region can comprise a second hot melt adhesive.

The elastic region allows the fastening tab area to stretch while the second bonded regions can add strength to the fastening tab area.

The second hot melt adhesive can be stiffer (i.e. have a higher modulus) than the elastic hot melt adhesive.

Figure 2:
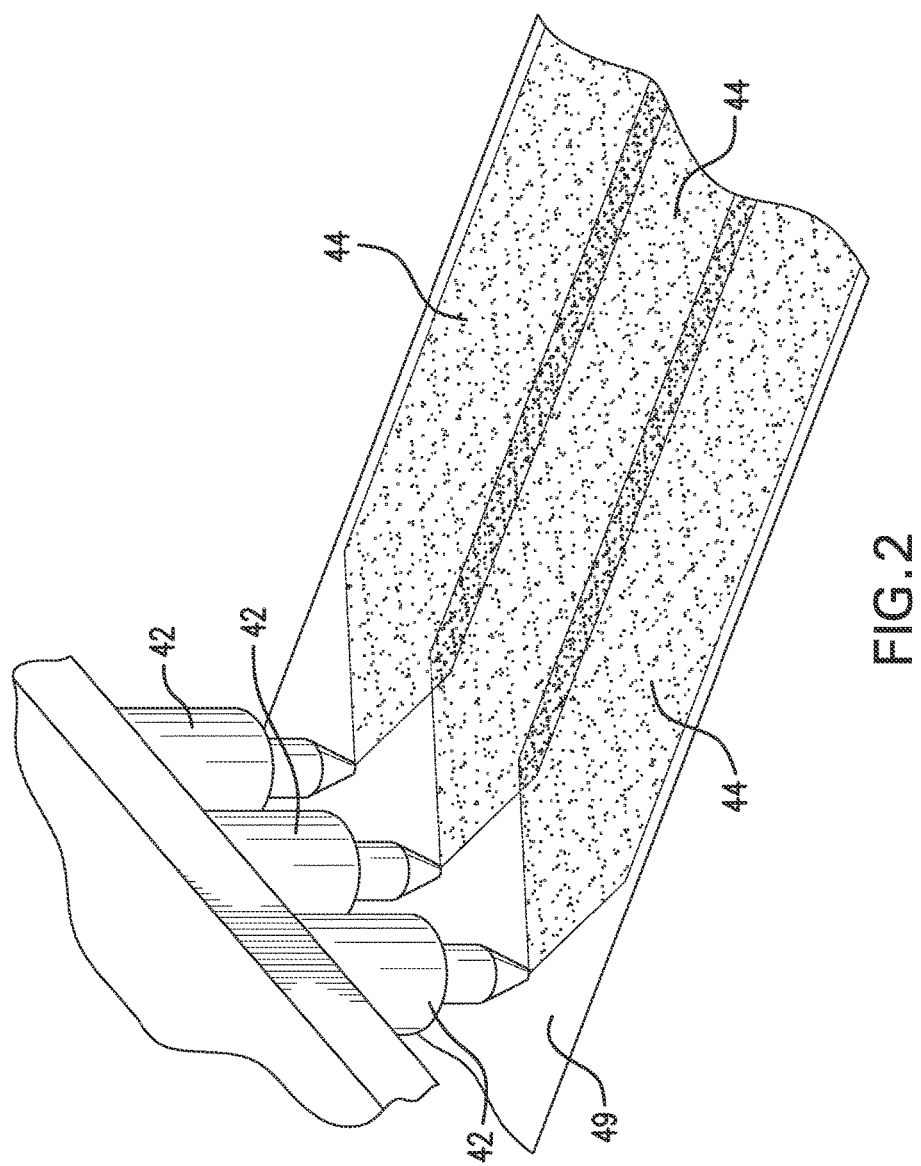
FIG. 2 is an illustration of how three adjacent bonded regions could be applied to a substrate using three different coating heads.

The hot melt adhesives can applied using two or more different coating heads using a slot coating or non-contact coating application to one substrate, forming a series of side by side continuous films that can be used to bond the first and second substrates together and create the bonded regions. In one embodiment (FIG. 2), three coating heads (42) are used to apply 3 adjacent adhesive regions (44), that slightly overlap each other, to a substrate (49).

Absorbent Undergarments

Figure 3:
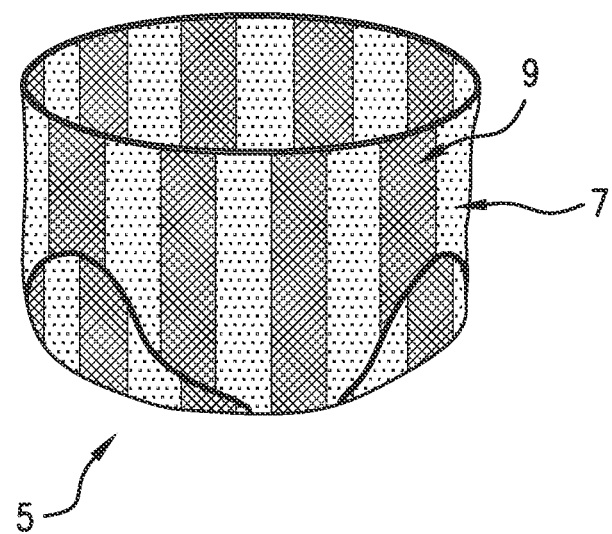
FIG. 3 is a front view of a absorbent undergarment with adjacent bonded regions present in a vertical stripe pattern throughout undergarment.

The adjacent bonded regions of this invention can be useful in creating absorbent undergarments that have the feel and stretch of cotton while being capable of absorbing body fluids. In one embodiment (FIG. 3), the absorbent undergarment (5) includes adjacent bonded regions that are present in a vertical stripe pattern throughout the absorbent article, elastic regions (7) alternating with second bonded regions (9). These vertical stripes can be more like a pin stripe; alternatively the vertical stripes can be wider. Individual stripes may be of the same or differing widths. The vertical stripes can have a width of from about 1 mm to about 100 mm, from about 1 mm to about 50 mm or even from about 2-25 mm.

The second bonded regions can comprise a second hot melt adhesive that introduces certain properties into the disposable absorbent article. The second hot melt adhesive can provide breathability, cohesion, stiffness, and/or lower creep. In one embodiment, breathability is introduced by coating one or both hot melt adhesives in a discontinuous manner.

EXAMPLES

Composition amounts in tables are all in weight %.
Test Procedures

Test procedures used in the examples and throughout the specification, unless stated otherwise, include the following.
Viscosity Test Method Viscosity is determined in accordance with ASTM D-3236 entitled, "Standard Test Method for Apparent viscosity of Adhesives and Coating Materials," (Oct. 31, 1988), using a Brookfield Thermosel viscometer Model RVDV 2 and a number 27 spindle. The results are reported in centipoise (cps).
Molten Gardner Color The hot melt adhesive is tested (in the molten state) to determine Molten Gardner Color by comparing the color of the sample against the Gardner Color Standards as set forth in ASTM D-1544. The comparison is made using a Gardner Delta. Comparator equipped with an illuminator available from Pacific Scientific (Bethesda, Md.).
Test Lamination Preparation Test laminations were prepared by continuous slot coating the elastic hot melt adhesive composition between two nonwoven* substrates at an application temperature of 177° C. (350° F.), a nip pressure of 10.5 Newtons/centimeter (N/cms) (6 pounds per linear inch (PLI)), and a run speed of at least 6.1 meters/min (m/min) (20 feet/min). Laminations were prepared with an adhesive coat weight of 100 grams per square meter (gsm) and the width of the adhesive was at least 7.6 cms (3 inches). A sufficient amount of laminate was prepared such that at least 1.5 m (60 inches) of representative lamination was collected for testing.

*The nonwoven used is carded, hydroentangled and comprises 50/50 (PET/PP). It has a basis weight of 29 g/m$^2$, a cross direction tensile strength of 93 grams/cm$^2$ (600 grams/in$^2$), a CD elongation at break=217% WSP Method 110.4, and an elongation ratio (CD/MD)=4.3.

Peel Force Test Method

Test laminates were prepared by coating elastic hot melt adhesive between two substrates according to the Test Lamination Preparation method above. Peel force is determined using ASTM D1876-01 entitled; "Test Method for Determining Peel Resistance of Adhesive (T-Peel Test Method)," with the exception that the test is run at a rate of 30.5 cms per minute (12 inches per minute), instead of 25.4 cms per minute (10 in per minute), over a period of 10 seconds, and 7 replicates are run instead of the 10 specified in ASTM D1876. The samples are run on an INSTRON type-test instrument. The test samples are 2.54 cms (1 inch) in width and at least 10.16 cms (4 inches) in length. The average peel force over 10 seconds of peeling is recorded, and the results are reported in grams. The initial peel force is measured at least 24 hours after the laminate is prepared.
2-Peak Hysteresis Test Method Test laminates were prepared by coating elastic hot melt adhesive between two substrates according to the Test Lamination Preparation method above. Test samples are prepared by cutting the laminates in cross-web direction, with 1 inch in width and at least 3 inches in length. The test is conducted at least 24 hours after the non-woven laminate is prepared.

The strips prepared are extended to a certain strain (e.g. 50%, 100%, 150% or 200%) and then retracted to their original dimension. Subsequently the specimen goes through a second extension-retraction cycle with the same deformation. The cross head speed is set to 50.8 cms per minute (20 inches per minute). There is no holding time between extension and retraction. The samples are run on an INSTRON type-test instrument with at least 3 replicates. The permanent set after each cycle is determined by the tensile strain on the retraction curve where the tensile stress reduces to 5 gram force. The peak load/stress at maximum deformation and percent energy loss between each cycles are also recorded.
Rheological Creep and Recovery Rheological Creep and Recovery was run on a Texas Instruments AR-G2 rheometer using parallel plate geometry with a 8 mm plate. The test was run isothermally at 38° C. with a gap of 300 um.

Once equilibrated at 38° C., a pressure of 26,800 Pa was applied. The sample was held at this pressure for 20 minutes (creep portion of test). The pressure was then released to 0 Pa for 20 minutes (recovery portion of test).

The strain was measured. Values at specified intervals are reported in the table.

TABLE ONE

|  | Comparative 1 | Comparative 2 |
|---|---|---|
| VECTOR 8508 (Avg. MFR (200° C./5 kg) = 12) | 40 | 45 |
| ESCOREZ 5615 | 49.5 | 29.5 |
| CALSOL 550 | 10 | 25 |
| IRGANOX 1010 | 0.5 | 0.5 |
| Viscosity @ 177° C. (350° F.) (cps) | 43,400 | 30,870 |

Comparative 1 and 2 are compositions outside of the inventive ranges. Both have a viscosity at 177° C. (350° F.) of greater than 15,000 cps and would not be expected to apply well on a high speed production line.

TABLE TWO

Elastic Hot Melt Adhesive Examples

|  | Ex. 1 | Ex. 2 | Ex. 3 | Ex. 4 | Ex. 5 | Ex. 6 |
|---|---|---|---|---|---|---|
| VECTOR 6241 |  |  |  |  |  | 20 |
| VECTOR 4411 | 46 | 46 | 46 | 42.5 | 42.5 | 26 |
| ESCOREZ 5490 |  |  |  | 32 |  |  |
| ESCOREZ 5400 | 33.5 |  |  |  |  |  |
| ESCOREZ 5690 |  | 33.5 | 33.5 |  | 32 | 31.5 |
| PURETOL 35 | 20 | 20 |  | 25 |  |  |
| CALSOL 550 |  |  | 20 |  | 25 | 22 |
| PLENISH |  |  |  |  |  |  |
| IRG 1010 | 0.5 | 0.5 | 0.5 | 0.5 | 0.5 | 0.5 |
| Viscosity (cps) |  |  |  |  |  |  |
| @149° C. (300° F.) | 204,500 | 68,000 | 38,800 | 77,000 | 18,250 | 33,500 |
| @163° C. (325° F.) | 14,050 | 9,700 | 8,020 | 6,950 | 4,210 | 8,940 |
| @177° C. (350° F.) | 14.56 | 7.01 | 4.83 | 11.10 | 4.34 | 3.75 |
| Rheo. Creep |  |  |  |  |  |  |
| Strain @ 0.01 sec |  |  |  | .078 | .067 |  |
| Strain @ 600 sec |  |  |  | .232 | .169 |  |
| Strain @ 1200 sec |  |  |  | .246 | .192 |  |
| Rheo. Recovery |  |  |  |  |  |  |
| Strain @ 1200 sec |  |  |  | .246 | .192 |  |
| Strain @ 1800 seconds |  |  |  | .05 | .041 |  |
| Strain @ 2400 sec |  |  |  | .043 | .033 |  |

|  | Ex. 7 | Ex. 8 | Ex. 9 | Ex. 10 | Ex. 11 |
|---|---|---|---|---|---|
| VECTOR 6241 | 20 |  |  |  |  |
| VECTOR 4411 | 26 | 50 | 50 | 35 | 35 |
| ESCOREZ 5490 | 29.5 | 29.5 |  | 38.5 |  |
| ESCOREZ 5400 |  |  |  |  |  |
| ESCOREZ 5690 | 31.5 |  | 29.5 |  | 38.5 |
| PURETOL 35 |  | 20 |  | 26 |  |
| CALSOL 550 |  |  | 20 |  | 26 |
| PLENISH | 22 |  |  |  |  |
| IRG 1010 | 0.5 | 0.5 | 0.5 | 0.5 | 0.5 |

TABLE TWO-continued

Elastic Hot Melt Adhesive Examples

| Viscosity (cps) | | | | | |
|---|---|---|---|---|---|
| @149° C. (300° F.) | 28,100 | 279,600 | 74,800 | 18400 | 6000 |
| @163° C. (325° F.) | 7,750 | 30,150 | 12,550 | 2545 | 2065 |
| @177° C. (350° F.) | 3.63 | 9.27 | 6.0 | 7.23 | 2.91 |
| Rheo. Creep | | | | | |
| Strain @ 0.01 sec | | | .052 | .084 | .078 |
| Strain @ 600 sec | | | .162 | .457 | .377 |
| Strain @ 1200 sec | | | .189 | .488 | .424 |
| Rheo. Recovery | | | | | |
| Strain @ 1200 sec | | | .189 | .488 | .424 |
| Strain @ 1800 seconds | | | .048 | .106 | .104 |
| Strain @ 2400 sec | | | .039 | .094 | .087 |

TABLE THREE

Elastic Hot Melt Adhesive Examples

| | Ex. 12 | Ex. 13 | Ex. 6 | Ex. 14 | Ex. 15 | Ex. 16 | Ex. 17 |
|---|---|---|---|---|---|---|---|
| VECTOR 8508 | 20 | 15 | | | | | |
| VECTOR 4411 | 26 | 31 | 26 | 26 | | 46.5 | |
| VECTOR 6241 | | | 20 | 20 | 30 | | 46.5 |
| GLOBALPRENE 3545 | | | | | 15 | | |
| Avg. Styrene Content of SBC | 37.5 | 39.1 | 43.6 | 43.6 | 43.7 | 44 | 43 |
| Avg. MFR (200° C./5 kg) | 27.8 | 30.9 | 32.6 | 32.6 | >33 | 40 | 23 |
| ESCOREZ 5690 | 31.5 | 31.5 | 31.5 | 33.5 | | 29.75 | 29.75 |
| ESCOREZ 5615 | | | | | 34.5 | | |
| CALSOL 550 | 22 | 22 | 22 | 20 | 20 | 23.25 | 23.25 |
| IRGANOX 1010 | 0.5 | 0.5 | 0.5 | 0.5 | 0.5 | 0.5 | 0.5 |

TABLE FOUR

| | Ex. 12 | Ex. 13 | Ex. 6 | Ex. 14 | Ex. 15 | Ex. 16 | Ex. 17 |
|---|---|---|---|---|---|---|---|
| Viscosity (cps) | | | | | | | |
| @149° C. (300° F.) | 47,000 | 48,590 | 33,500 | 33,000 | 33,800 | 35,150 | 37,800 |
| @163° C. (325° F.) | 23,125 | 21,570 | 16,290 | 16,150 | 17,750 | 14,250 | 18,850 |
| @177° C. (350° F.) | 12,700 | 12,800 | 8,940 | 9,250 | 11,050 | 7,050 | 12,050 |
| Viscosity Ratio@ 149° C./177° C. | 3.70 | 3.80 | 3.75 | 3.56 | 3.06 | 4.99 | 3.11 |

TABLE FOUR-continued

|  | Ex. 12 | Ex. 13 | Ex. 6 | Ex. 14 | Ex. 15 | Ex. 16 | Ex. 17 |
|---|---|---|---|---|---|---|---|
| Elasticity | | | | | | | |
| 50% hysteresis | | | | | | | |
| Set $1^{st}$ cycle (%) | 6 | 6 | 6 | 8 | 9 | 6 | 5 |
| Set $2^{nd}$ cycle (%) | 7 | 6 | 7 | 10 | 10 | 7 | 6 |
| Energy loss (%) | 31.1 | 31.1 | 35.1 | 37.0 | 37.9 | 35.1 | 34.5 |
| 100% hysteresis | | | | | | | |
| Set $1^{st}$ cycle (%) | 15 | 14 | 15 | 21 | 23 | 16 | 14 |
| Set $2^{nd}$ cycle (%) | 17 | 17 | 17 | 23 | 26 | 18 | 16 |
| Energy loss (%) | 43.0 | 44.2 | 46.7 | 48.7 | 51.2 | 46.9 | 45.6 |
| 150% hysteresis | | | | | | | |
| Set $1^{st}$ cycle (%) | 24 | 24 | 27 | 37 | 41 | 26 | 23 |
| Set $2^{nd}$ cycle (%) | 27 | 27 | 30 | 40 | 45 | 28 | 27 |
| Energy loss (%) | 54.3 | 55.1 | 55.2 | 59.8 | 61.6 | 56.2 | 54.4 |
| Adhesion | | | | | | | |
| Average peel (gram force) | 278 | 238 | 437 | 256 | 852 | 68 | 272 |

What is claimed is:

1. A disposable article comprising at least two adjacent bonded regions:
   the first bonded region, comprising:
   a first and second substrate; and an elastic hot melt adhesive composition between the first and second substrates thereby bonding the first and second substrates to each other; the elastic hot melt adhesive composition having a viscosity of less than about 15,000 cps at 350° F. and a set after 50% hysteresis of no greater than about 20%;
   the second bonded region comprising:
   a first substrate and second substrate; and a hot melt adhesive composition between the first substrate and second substrates thereby bonding the first substrate and second substrates to each other, the second bonded region having properties different from the first bonded region, the first and second substrate being selected from a group consisting of a nonwoven and a polymer film, and wherein the first and second bonded regions are free of non-adhesive elastic materials.

2. The disposable article of claim 1 wherein the at least two adjacent bonded regions comprise the same elastic hot melt adhesive applied at different coat weights.

3. The disposable article of claim 1 wherein the second bonded region comprises a second hot melt adhesive composition different from the elastic hot melt adhesive composition.

4. The disposable article of claim 3 wherein the two different hot melt adhesives are applied to the substrate using two different application methods.

5. The disposable article of claim 1 wherein the disposable article is a disposable absorbent article.

6. The disposable article of claim 5 wherein the at least two adjacent bonded regions are used in a application selected from the group consisting of fastening ear, waist band, belly band and side panel.

7. The disposable article of claim 6 wherein three adjacent bonded regions make up the fastening ear; the three adjacent bonded regions comprising an elastic bonded region between two second bonded regions.

8. The disposable article of claim 5 selected from the group consisting of diaper, absorbent undergarment, feminine hygiene product and medical bandage.

9. The absorbent undergarment of claim 8 comprising adjacent bonded regions throughout the absorbent undergarment, the adjacent bonded regions comprising elastic bonded regions alternating with second bonded regions.

10. The disposable article of claim 1 wherein on least one of the substrates is nonwoven.

11. The disposable article of claim 10 wherein the nonwoven is airlaid, carded and hydroentangled.

12. The elastic composite of claim 10 wherein the nonwoven is extensible to greater than 100% in the cross web direction.

13. The disposable article of claim 1 wherein the elastic hot melt adhesive composition comprises:
   about 30% by weight to about 60% by weight of one or more styrene block copolymers wherein the one or more styrene block copolymers has an average styrene content of at least about 30% by weight and an average Melt Flow Rate (MFR) according to ASTM D 1238 (200° C./5 kg) in dg/min of no less than about 20,
   greater than about 10% of a plasticizer and,
   a tackifying agent.

14. The disposable article of claim 13 wherein the elastic hot melt adhesive composition comprises:
   a tackifying agent that is a hydrocarbon resin with about 5% to about 20% by weight of aromatic content, and;
   a plasticizer that is a naphthenic oil.

15. The disposable article of claim 13 wherein the average styrene content of the one or more styrene block copolymers is at least about 40% by weight.

16. The disposable article of claim 13 wherein the one or more styrene block copolymers has an average MFR (200° C./5 kg) of no less than about 30.

17. The disposable article of claim 1 wherein at least one of the hot melt adhesives is applied to the substrate using an application method selected from the group consisting of slot and non contact coating.

18. The disposable article of claim 1 wherein at least one of the hot melt adhesives is applied to the substrate using an application method selected from the group consisting of screen printing, spraying, comb shim slot and gravure roll.

19. A disposable article comprising at least one layered bonded region, the layered bonded region comprising:
   a first substrate,
   an elastic hot melt adhesive composition coated in a continuous coating on the first substrate, a second hot melt adhesive composition coated in a discontinuous manner on the elastic hot melt adhesive, and a second substrate;

wherein the second substrate is bonded to the elastic hot melt adhesive composition through the second hot melt adhesive composition; the elastic hot melt adhesive composition having a viscosity of less than about 15,000 cps at 350° F. and a set after 50% hysteresis of no more than about 20%;

the first and second substrate being selected from a group consisting of a nonwoven and a polymer film, and wherein the layered bonded region is free of non-adhesive elastic materials.

* * * * *